United States Patent
Ranchod et al.

(10) Patent No.: US 10,610,094 B2
(45) Date of Patent: Apr. 7, 2020

(54) MULTIPLE OFF-AXIS CHANNEL OPTICAL IMAGING DEVICE WITH SECONDARY FIXATION TARGET FOR SMALL PUPILS

(71) Applicant: BROADSPOT IMAGING CORP, Richmond, CA (US)

(72) Inventors: Tushar M. Ranchod, Berkeley, CA (US); Benjamin A. Jacobson, Santa Barbara, CA (US); Clark Pentico, Simi Valley, CA (US)

(73) Assignee: BROADSPOT IMAGING CORP, Richmond, CA (US)

( * ) Notice: Subject to any disclaimer, the term of this patent is extended or adjusted under 35 U.S.C. 154(b) by 0 days.

(21) Appl. No.: 16/224,292

(22) Filed: Dec. 18, 2018

(65) Prior Publication Data

US 2019/0200856 A1    Jul. 4, 2019

Related U.S. Application Data

(60) Provisional application No. 62/611,085, filed on Dec. 28, 2017.

(51) Int. Cl.
*A61B 3/10* (2006.01)
*A61B 3/00* (2006.01)
(Continued)

(52) U.S. Cl.
CPC .............. *A61B 3/0091* (2013.01); *A61B 3/12* (2013.01); *A61B 3/14* (2013.01)

(58) Field of Classification Search
CPC ... A61B 3/0025; A61B 3/0058; A61B 3/0075; A61B 3/0083; A61B 3/0091;
(Continued)

(56) References Cited

U.S. PATENT DOCUMENTS

| 4,923,297 A | 5/1990 | Arndt |
| 7,140,730 B2 | 11/2006 | Wei et al. |

(Continued)

FOREIGN PATENT DOCUMENTS

WO    02/007068 A1    1/2002

OTHER PUBLICATIONS

Götzinger et al. "Polarization maintaining fiber based ultra-high resolution spectral domain polarization sensitive optical coherence tomography" Opt. Express, vol. 17(25), pp. 22704-22717; Dec. 7, 2009.

(Continued)

*Primary Examiner* — Mustak Choudhury

(74) *Attorney, Agent, or Firm* — Maschoff Brennan

(57) ABSTRACT

An optical imaging device includes a plurality of imaging channels. Each imaging channel of the plurality of imaging channels may include a discrete optical imaging pathway, and the plurality of imaging channels may be disposed within a support structure. The plurality of imaging channels may be aimed at different angles relative to each other. The optical imaging device may also include a secondary fixation target within at least one imaging channel of the plurality of imaging channels such that at least one corresponding optical imaging pathway fits through a pupil diameter that is smaller than a minimum pupil diameter for multi-channel image acquisition with primary fixation.

20 Claims, 9 Drawing Sheets

(51) Int. Cl.
*A61B 3/12* (2006.01)
*A61B 3/14* (2006.01)

(58) Field of Classification Search
CPC ......... A61B 3/024; A61B 3/028; A61B 3/085;
A61B 3/10–14; A61B 3/102; A61B
3/107; A61B 3/113; A61B 3/117; A61B
3/132; A61B 3/135; A61B 3/145; A61B
3/152; A61B 3/158; A61B 3/165; A61B
3/1015; A61B 3/1025; A61B 3/1202;
A61B 3/1208; A61B 3/1225; A61B
5/0066; A61B 5/04842; A61B 5/14555;
A61F 2009/00846; G06K 9/00604; G01J
9/02; G01B 9/02007; G01B 9/02027;
G01B 9/02039; G01B 9/02041; G01B
9/02044; G01B 9/02048; G01B 9/02087;
G01B 9/02091
USPC ......... 359/200–208, 210–223, 246; 356/450,
356/512; 348/78, E7.085
See application file for complete search history.

(56) References Cited

U.S. PATENT DOCUMENTS

| | | | |
|---|---|---|---|
| 7,854,510 B2 | 12/2010 | Verdooner et al. | |
| 8,714,743 B2 | 5/2014 | Verdooner | |
| 8,807,751 B2 | 8/2014 | Kahn et al. | |
| 9,295,388 B2 | 3/2016 | Lawson et al. | |
| 9,314,155 B2 | 4/2016 | Verdooner | |
| 9,480,394 B2 | 11/2016 | Verdooner | |
| 9,521,950 B2 | 12/2016 | Verdooner | |
| 2005/0286019 A1 | 12/2005 | Wiltberger et al. | |
| 2009/0153796 A1 | 6/2009 | Rabner | |
| 2010/0195048 A1 | 8/2010 | Hammer et al. | |
| 2011/0234978 A1 | 9/2011 | Hammer et al. | |
| 2012/0249957 A1 | 10/2012 | Shibata et al. | |
| 2012/0287255 A1* | 11/2012 | Ignatovich | A61B 3/1208 348/78 |
| 2013/0033593 A1 | 2/2013 | Chinnock et al. | |
| 2013/0107277 A1 | 5/2013 | Hirose et al. | |
| 2013/0250243 A1* | 9/2013 | Cech | A61B 3/12 351/208 |
| 2013/0271728 A1* | 10/2013 | Ranchod | A61B 3/14 351/206 |
| 2016/0135679 A1 | 5/2016 | Frisken et al. | |
| 2017/0314908 A1 | 11/2017 | Chong | |

OTHER PUBLICATIONS

International Search Report dated Apr. 1, 2019 as received in Application No. PCT/US2018/067399.

Written Opinion of the International Searching Authority dated Apr. 1, 2019 as received in Application No. PCT/US2018/067399.

\* cited by examiner

MULTIPLE OFF-AXIS CHANNEL OPTICAL IMAGING DEVICE WITH SECONDARY FIXATION TARGET FOR SMALL PUPILS

FIELD

The application relates generally to a multiple off-axis channel optical imaging device with a secondary fixation target for small pupils.

BACKGROUND

Ocular imaging is commonly used both to screen for diseases and to document findings discovered during clinical examination of the eye. Specifically, documentation and analysis of optical imaging may be relevant to comprehensive eye examinations and full evaluations of current conditions, treatment, and/or early prevention of various eye conditions and diseases. Pupil size may affect optical imaging.

The subject matter claimed herein is not limited to embodiments that solve any disadvantages or that operate only in environments such as those described above. Rather, this background is only provided to illustrate one example technology area where some embodiments described herein may be practiced.

SUMMARY

Embodiments of the disclosure discuss an optical imaging device. The optical imaging device may include multiple imaging channels, where each imaging channel may include a discrete optical imaging pathway disposed within a support structure. In these embodiments, the imaging channels may be aimed at different angles relative to each other. The optical imaging device may additionally include a secondary fixation target within at least one imaging channel such that at least one corresponding optical imaging pathway fits through a pupil diameter that is smaller than a minimum pupil diameter for multi-channel image acquisition with primary fixation.

The objects and advantages of the embodiments will be realized and achieved at least by the elements, features, and combinations particularly pointed out in the claims.

Both the foregoing general description and the following detailed description are given as examples and are explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

In some embodiments of the present disclosure, imaging channels, each with at least one unique imaging pathway, may approach the eye at different angles. The respective imaging pathways may cross each other within the plane of the iris of the human eye, or within the space between the cornea and the mid-vitreous cavity, or at any point between the retina and the cornea. In these or other embodiments, none of the imaging channels may be coaxial with a central axis of the eye. However, in some embodiments, at least one imaging channel may be coaxial with the central axis of the eye. The imaging channels may image different but partially overlapping regions of the eye such that the resulting images may be stitched into a single composite optical image with a combined area greater than any constituent image and in such a way that gaps may not appear within the composite image. For example, a first image may correspond to a first optical region; a second image may correspond to a second optical region; and a third image may correspond to a third optical region. In this example, each region may be overlapped by at least one other region. Continuing with the example, the three example images may be gathered, and the overlap regions may be averaged or homogenized for clarity and continuity thereby helping to create a single contiguous image of all three regions based on the three individual images. In these or other embodiments, images (whether individual images or composite images) may be stored in a storage device coupled to the optical imaging device. In these or other embodiments, more or fewer than three images may comprise a composite image.

In some embodiments of the present disclosure, a secondary fixation target may be implemented in addition to or in place of a primary fixation target. For example, in the event a pupil of the eye to be imaged does not dilate beyond a threshold amount, image acquisition using the primary fixation target may result in a smaller portion of the eye that may be imaged due to obstruction of optical imaging pathways, e.g., by an iris portion of the eye. Accordingly, the secondary fixation target may help to more favorably position at least one imaging channel relative to the eye such that a greater portion of the eye may be imaged.

Figure 1A:
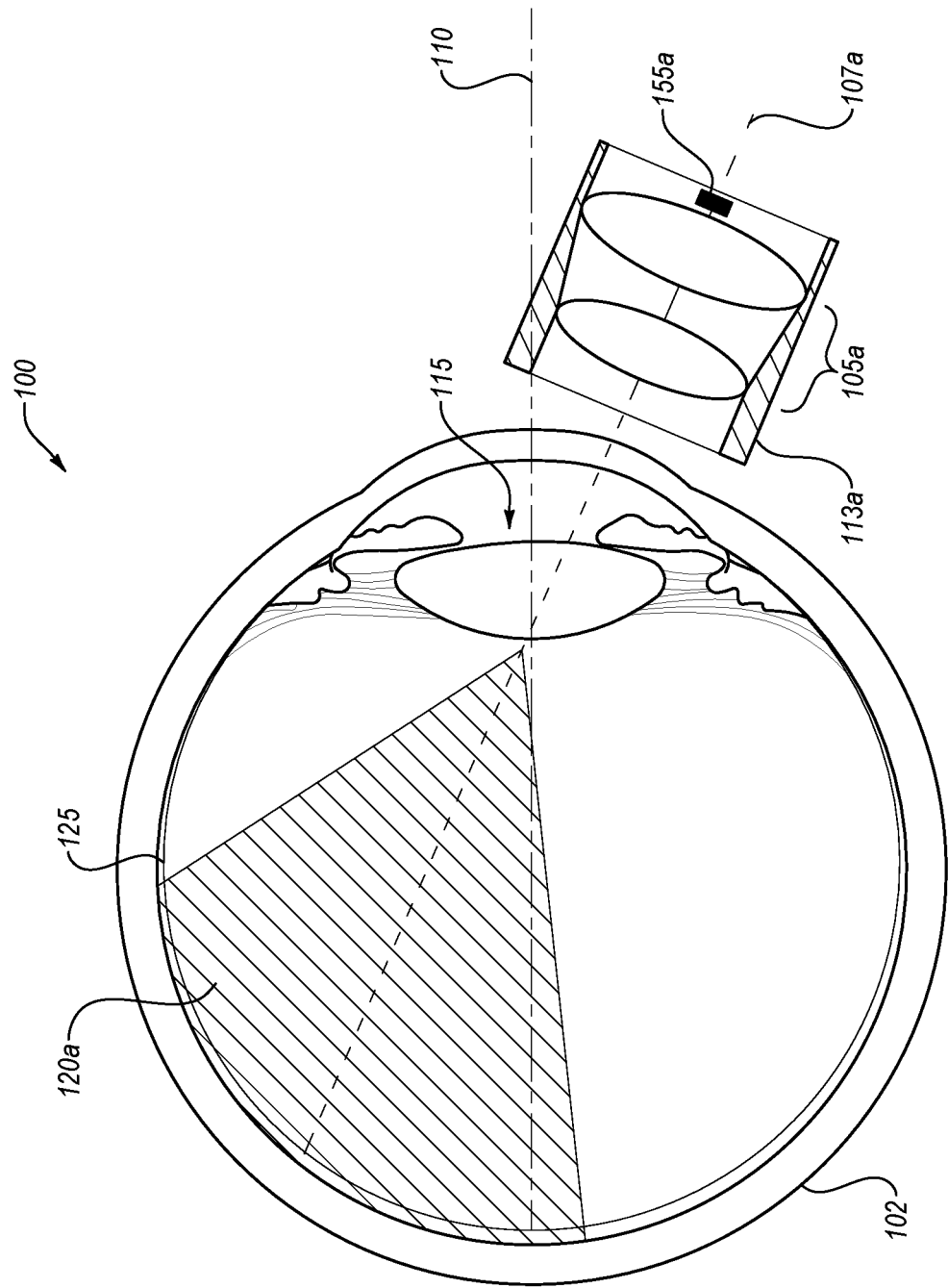
FIG. 1A illustrates a cross-sectional side view of an eye, including an example optical imaging pathway for imaging the eye.
Figure 1B:
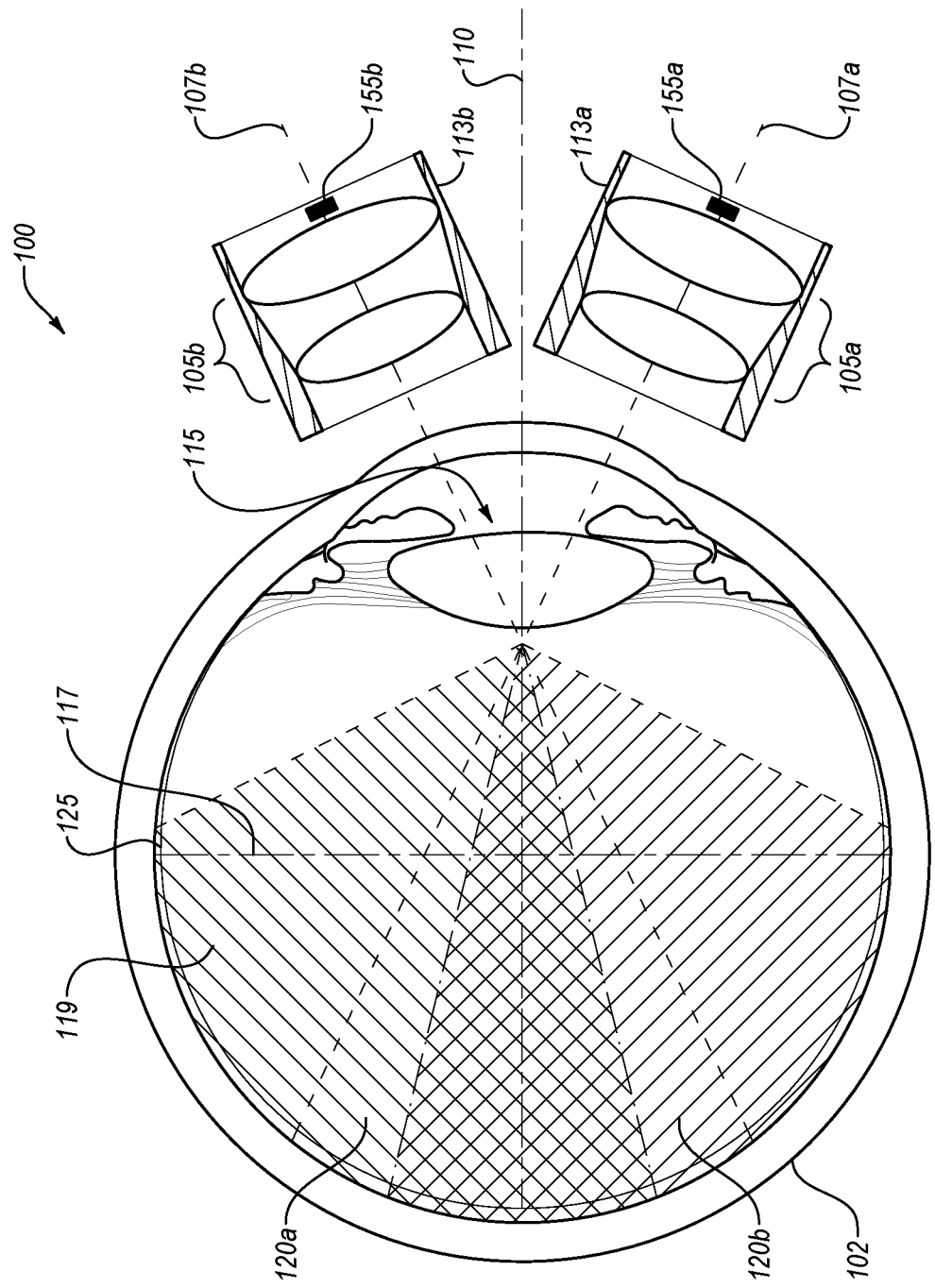
FIG. 1B illustrates another cross-sectional side view of the eye of FIG. 1A, including multiple example optical imaging pathways.
Figure 1C:
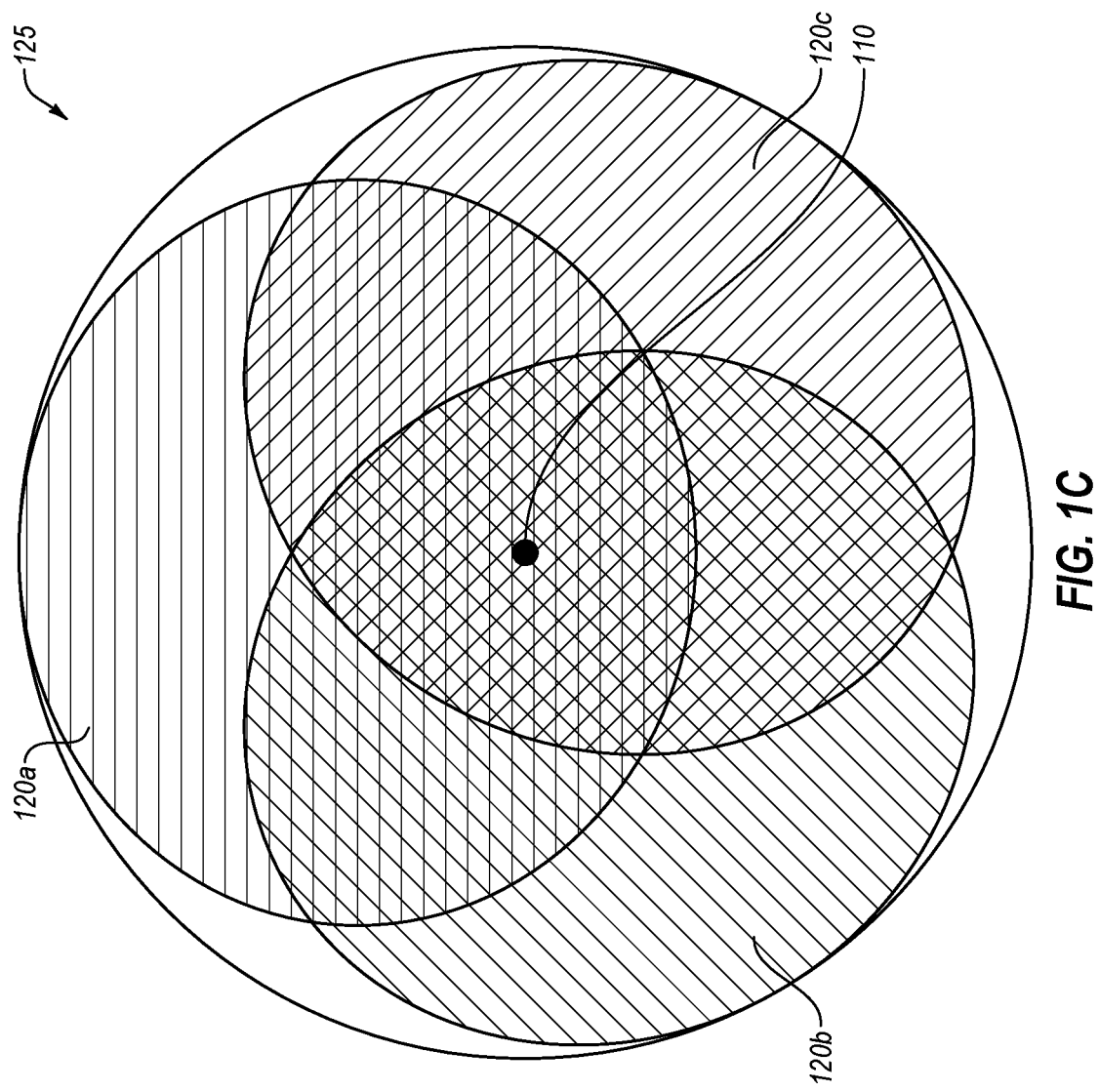
FIG. 1C illustrates a cross-sectional front view of the eye of FIG. 1A, including multiple overlapping imaging regions of the eye.

FIGS. 1A-1C indicate an example progression for achieving a composite optical image. For example, FIG. 1A illustrates a cross-sectional side view of an eye 102, including an example optical imaging pathway 107a for imaging the eye 102. FIG. 1B illustrates the same cross-sectional side view of the eye 102 with the addition of a second example optical imaging pathway 107b for imaging the eye 102. FIG. 1C illustrates three overlapping imaging regions 120a, 120b, and 120c for imaging an example area of the eye 102, including a retina 125. FIG. 1A also illustrates an imaging channel 113a, an eye lens 115, optical lenses 105a, a central axis 110, an imaging region 120a, and an image capturing device 155a. In these or other embodiments, the optical imaging pathway 107a may proceed from within the imaging channel 113a of a device (such as the optical imaging device 200/300/400 respectively illustrated in FIGS. 2A/2B, FIGS. 3A-3B, and FIG. 4), through the pupil and the eye lens 115, and to the retina 125. Additionally or alternatively, the optical imaging pathway 107a may start and/or end at the image capturing device 155a, and the image capturing device 155a may be positioned anywhere within the imaging channel 113a. For example, the imaging capturing device 155a may be positioned between the optical lenses 105a, along a central axis of the imaging channel 113a normal to the eye 102, and/or off the central axis of the imaging channel 113a normal to the eye 102. In these or other embodiments, the optical imaging pathway 107a may be a center axis of a field of view of the image capturing device 155a. Additionally or alternatively, the imaging region 120a may correspond to the optical imaging pathway 107a. For example, an area of the retina 125 that is covered by or is adjacent to the optical imaging pathway 107a may define the metes and bounds of the imaging region 120a. In other embodiments, other areas of the eye 102, such as the cornea, the iris, the iridocorneal angle, the sclera, and any other suitable area of the eye 102, whether in the anterior or posterior chamber of the eye 102, may be imaged.

In some embodiments, the optical lenses 105a may be housed by the imaging channel 113a and may collimate illumination light proceeding through the imaging channel 113a such that the illumination light proceeds collinear with and/or parallel to the optical imaging pathway 107a and illuminates at least a portion of the imaging region 120a. In some embodiments, the optical lenses 105a may be sized and shaped to fill an inner diameter of the imaging channel 113a that houses the optical lenses 105a, while in other embodiments, the optical lenses 105a may be sized and shaped to be less than the inner diameter of the imaging channel 113a. Additionally or alternatively, the optical lenses 105a may focus, disperse, and/or otherwise alter light transmission to enhance imaging capability of the image capturing device 155a to image the imaging region 120a. In these or other embodiments, the image capturing device 155a may be an imaging device or sensor that may respectively include an entire imaging sensor or a portion of a larger digital camera, where the larger digital camera may be positioned outside of the optical imaging device.

In some embodiments, other optical elements may also be included within the imaging channel 113a. For example, a prism may be positioned anywhere within the imaging channel 113a, e.g., between the optical lenses 105a, at a distal end of the imaging channel 113a and/or at a proximal end of the imaging channel positioned between the eye 102 and the optical lenses 105a. In some embodiments, the prism may be configured as a mirror, beam splitter, or other suitable reflective element (e.g., partially reflective, substantially reflective, or completely reflective). In these or other embodiments, multiple prisms may be positioned within the imaging channel 113a, while in other embodiments, only a single prism within the imaging channel 113a. In some embodiments, the prism may help direct light to and/or from the eye 102, e.g., permitting multi-directional travel of optical signals between the eye 102 and an optical imaging device. For example, the prism may at least partially direct one or both of the optical imaging pathway 107a and an optical illumination pathway toward the eye 102.

In some embodiments, the optical imaging pathway 107a may not be coaxial to the central axis 110 of the eye 102. In this manner, multiple optical imaging pathways 107 (such as the optical imaging pathways 107a and 107b as shown in FIG. 1B) may enable imaging of the retina 125 and/or other areas of the eye 102, such as the cornea, the iris, the iridocorneal angle, the sclera, and any other suitable area of the eye 102, whether in the anterior or posterior chamber of the eye 102.

Additionally or alternatively, the optical lenses 105a may have fixed or variable positions within the imaging channel 113a. For example, one or more of the optical lenses 105a may be positionally fixed such that the optical lenses 105a may not move within the imaging channel 113a. As another example, one or more of the optical lenses 105a may be positionally movable within the imaging channel 113a such that the lenses may slide closer to the eye 102 during examination or slide farther away from the eye 102 during examination. Additionally or alternatively, the optical lenses 105a may be positionally movable within the imaging channel 113a such that the lenses may slide laterally so as to maintain a relative distance between the optical lenses 105a and the eye 102 during examination or image acquisition. Additionally or alternatively, the optical lenses 105a may be fixed positionally, but movable at the fixed position. For example, at least one of the optical lenses 105a may be angularly varied in orientation within the imaging channel 113a such that an angular orientation of the at least one optical lens 105a may be changed to or positioned at any angle such as perpendicular to the optical imaging pathway 107a, parallel to the optical imaging pathway 107a, and any suitable angle therebetween. In this manner, different imaging regions may be obtained and/or optical properties adjusted for lighting and/or imaging.

FIG. 1B illustrates another cross-sectional side view of the eye 102 of FIG. 1A, including multiple example optical imaging pathways 107 (such as the optical imaging pathways 107a and 107b) for imaging the retina 125 and/or other areas of the eye 102, such as the cornea, the iris, the iridocorneal angle, the sclera, and any other suitable area of the eye 102, whether in the anterior chamber or a posterior cavity 119 of the eye 102. Specifically, FIG. 1B shows the addition of an imaging channel 113b, an optical imaging pathway 107b, optical lenses 105b, overlapping imaging regions 120a/120b, and an image capturing device 155b.

The imaging channel 113b, the optical imaging pathway 107b, the optical lenses 105b, and the image capturing device 155b may be the same as or similar to the imaging channel 113a, the optical imaging pathway 107a, the optical lenses 105a, and the image capturing device 155a, respectively, of FIG. 1A. In some embodiments, more or fewer image capturing devices 155 may be utilized in the optical imaging device, e.g., depending on an imaging application or pupil size of the eye to be imaged.

Additionally or alternatively, the imaging channel 113b and/or the optical imaging pathway 107b may not be coaxial to the central axis 110 of the eye 102. Thus, in some embodiments, the optical imaging pathways 107 of the imaging channels 113 may be angled relative to each other and/or to the central axis 110. For example, in some embodiments, the optical imaging pathways 107 may cross each other at a position within the posterior cavity 119 of the eye 102, and at a position anterior to an equatorial line 117, e.g., when imaging the retina 125. In other embodiments, depending on the desired target area of the eye 102 to be imaged, such as a surface of the cornea, the iris, the iridocorneal angle or the sclera, the optical imaging pathways 107 may converge at a position in the anterior chamber or at a position anterior to an outer surface of the cornea. In other embodiments, depending on the desired target area of the eye 102 to be imaged, the optical imaging pathways 107 may converge at a position in the posterior cavity 119 of the eye 102, and at a position posterior to an equatorial line 117.

In these or other embodiments, the imaging region 120a may correspond to the optical imaging pathway 107a, and the imaging region 120b may correspond to the optical imaging pathway 107b. The imaging regions 120a/120b may include portions of, for example, the retina 125 that are captured in digital images. Additionally or alternatively, the imaging region 120a and the imaging region 120b may overlap, for example, such that one or more portions of the retina 125 are captured in both images through the imaging channels 113a and 113b.

In some embodiments, imaging channels 113 may be fixed relative to each other, exactly or approximately, in terms of position in three-dimensional space or in terms of angles relative to a central optical axis of each imaging channel or the central axis 110 of the eye 102. For example, the imaging channels 113 may be angled at approximately equal angles off of the central optical axis of each imaging channel 113. Additionally or alternatively, the imaging channels 113 may be angled at approximately equal angles off of the central axis 110 of the eye 102 of the patient such that the imaging channels 113 may be evenly spaced in the 360 degrees around the central axis 110 of the eye 102 (e.g., each imaging channel 113 offset by approximately 30 degrees to approximately 45 degrees from the central axis 110 of the eye 102 and/or distributed approximately 120 degrees relative to each other).

In some embodiments, the angles between the imaging channels 113 relative to the central optical axis of each imaging channel 113 or relative to the central axis 110 of the eye 102 may not be equal or consistent. For example, different angles may accommodate different configurations and shapes of facial structures (e.g., a triangular base other than an equilateral triangle may be incorporated). In these or other embodiments, various configurations and numbers of imaging channels 113 may be used. For example, in some embodiments, four or five imaging channels 113 may be used in the optical imaging device 300 (not shown), while in other embodiments, between six and ten imaging channels 113 may be used, while in still other embodiments, only two imaging channels 113 may be used.

In some embodiments, the known relative positioning of the multiple imaging channels 113 may facilitate the stitching of multiple images into a composite image via software analytics. Thus, according to some embodiments, regardless of the angles (equal or not) of the imaging channels 113 relative to the central axis 110 of the eye 102 or relative to the central optical axis of each imaging channel, the angles may be known variables to the software such that image stitching may be achieved with sufficient precision. The multiple images to be stitched into a composite image, which are obtained via the image capturing devices 155 within the imaging channels 113, may be stored in a storage device.

FIG. 1C illustrates a cross-sectional front view of the eye 102 of FIG. 1A, including multiple overlapping imaging regions 120a/120b/120c of the retina 125. In other embodiments, the multiple overlapping imaging regions 120a/120b/120c may correspond to other areas of the eye 102, such as the cornea, the iris, the iridocorneal angle, the sclera, and any other suitable area of the eye 102, whether in the anterior chamber or a posterior cavity 119 of the eye 102. With the three different but overlapping imaging regions 120a/120b/120c of, for example, the retina 125, a composite image may be obtained that includes a combined area with a greater field of view than any single imaging region 120 and with fewer or no gaps within the composite image area. In some embodiments, the central axis 110 of the eye 102 may intersect a position on the retina 125 that is within two or more of the imaging regions 120.

In these or other embodiments of the present disclosure, an optical imaging device (such as that shown in FIG. 3) may include an upside-down pyramidal configuration of imaging channels 113 for increasing a clearance distance relative to facial structures of patients. In other embodiments, additional configurations of the imaging channels 113, other than for an upside-down pyramidal configuration of the optical imaging device, may be implemented. For example, any suitable configuration permitting additional or increased clearance between the optical imaging device and one or both of a bony brow and a nose is contemplated herein. Additionally or alternatively, any suitable configuration permitting multiple imaging channels 113, e.g., two or more imaging channels 113, for imaging the eye 102 may be implemented. Additional details may be provided in U.S. patent application Ser. No. 16/217,750 filed on Dec. 12, 2018, entitled MULTIPLE OFF-AXIS CHANNEL OPTICAL IMAGING DEVICE UTILIZING UPSIDE-DOWN PYRAMIDAL CONFIGURATION; and U.S. Provisional Patent Application No. 62/611,069 filed on Dec. 28, 2017, entitled MULTIPLE OFF-AXIS CHANNEL RETINAL IMAGING DEVICE WITH ROTATIONAL MONTAGE, the contents of both applications which are hereby incorporated by reference in their entirety.

Modifications, additions, or omissions may be made to the embodiments of FIGS. 1A-1C without departing from the scope of the present disclosure. For example, in some embodiments, the channels 113a/113b may include any number of other components that may not be explicitly illustrated or described. Additionally or alternatively, for example, the imaging regions 120a/120b/120c may include different sizes, shapes, overlapping areas, etc. than may be explicitly illustrated or described.

Figure 2A:
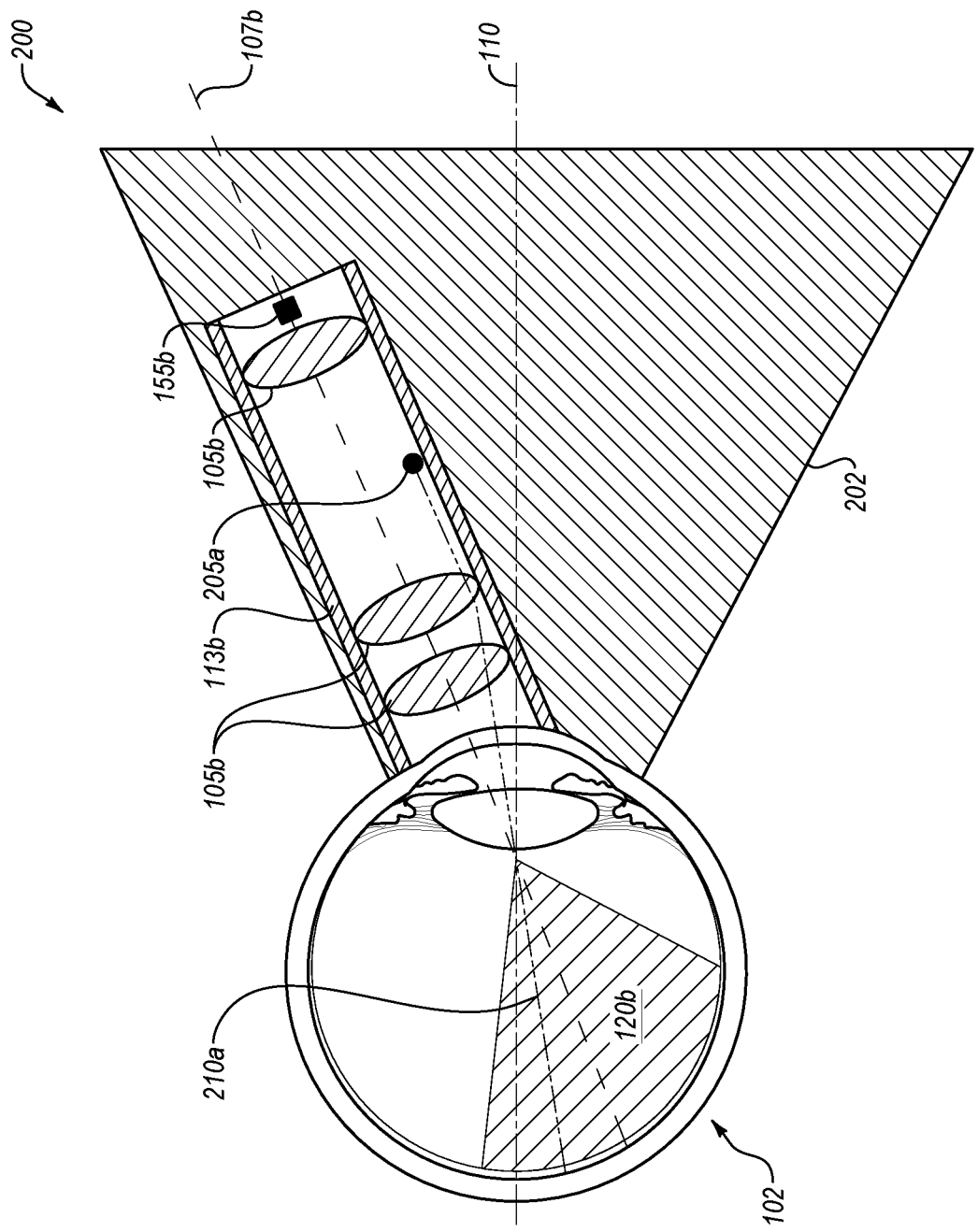
FIG. 2A illustrates an example embodiment of a cross-sectional side view of an optical imaging device using primary fixation for imaging the eye.

FIG. 2A illustrates an example embodiment of a cross-sectional side view of an optical imaging device 200 using primary fixation for imaging the eye 102, all arranged according to one or more embodiments of the present disclosure. As illustrated, the optical imaging device 200 includes the optical lenses 105b, the optical imaging pathway 107b, the imaging channel 113b, and the image capturing device 155b of FIGS. 1A-1B. Additionally, FIG. 2A illustrates a support structure 202, a primary fixation target 205a, and a primary fixation target projection 210a.

The support structure 202 may house the optical lenses 105b, the imaging channels 113b, and the image capturing devices 155b. Additionally or alternatively, the support structure 202 may be sized and shaped for ergonomic purposes, e.g., to more suitably interface with facial features of a patient. In other embodiments, additional configurations of the support structure 202, other than a triangular shape or pyramidal configuration, may be implemented. For example, any suitable configuration permitting additional or increased clearance between the support structure 202 and one or both of a bony brow and a nose is contemplated herein. Additionally or alternatively, any suitable configuration permitting multiple imaging channels 113, e.g., two or more imaging channels 113, for imaging the eye 102 may be implemented.

In some embodiments, one or more of the optical lenses 105b may be a common lens that shares both the optical imaging pathway 107b and the primary fixation target projection 210a. However, in other embodiments, the primary fixation target 205a may be positioned within the imaging channel 113b in such a manner so as to not share any of the optical lenses 105b with the optical imaging pathway 107b.

In some embodiments, the primary fixation target projection 210a may correspond to the primary fixation target 205a. For example, the primary fixation target projection 210a may include an optical axis or an optical direction that optical signals produced by the primary fixation target 205a may be generally directed along. Additionally or alternatively, the primary fixation target projection 210a may include an optical pathway that optical signals produced by the primary fixation target 205a may generally follow. Obstruction of optical signals may alter an actual path of the optical signals produced by the primary fixation target 205a, and thus, in some embodiments, the primary fixation target projection 210a may not necessarily include an actual path of the optical signals, for example, all the optical signals, produced by the primary fixation target 205a. Some optical signals produced by the primary fixation target 205a may be blocked or obstructed along the primary fixation target projection 210a, e.g., by an iris 335 of FIG. 3A in small-pupil scenarios. In these or other embodiments, the primary fixation target projection 210a may proceed from the primary fixation target 205a, through one or more optical elements such as the optical lenses 105b, to the eye 102, e.g., onto a fovea of the eye 102.

In some embodiments, the primary fixation target 205a may be positioned anywhere within the imaging channel 113b. Additionally or alternatively, the primary fixation target 205a may be positioned outside of the imaging channel 113b, e.g., as shown for a primary fixation target 205b in FIG. 2B. In these or other embodiments, utilization of primary fixation and the primary fixation target 205a may result in a center axis of the support structure 202 being collinear with the central axis 110 of the eye 102. In these or other embodiments, the primary fixation target 205a may be a visual aid that the eye 102 of the patient can fixate upon. When the eye 102 fixates on the primary fixation target 205a, image acquisition of the eye may be performed by the image capturing device 155b. However as described in greater detail below, for example in conjunction with FIGS. 3A-3B, the primary fixation target 205a may be insufficient to favorably align the imaging channel 113b in small-pupil scenarios.

Figure 2B:
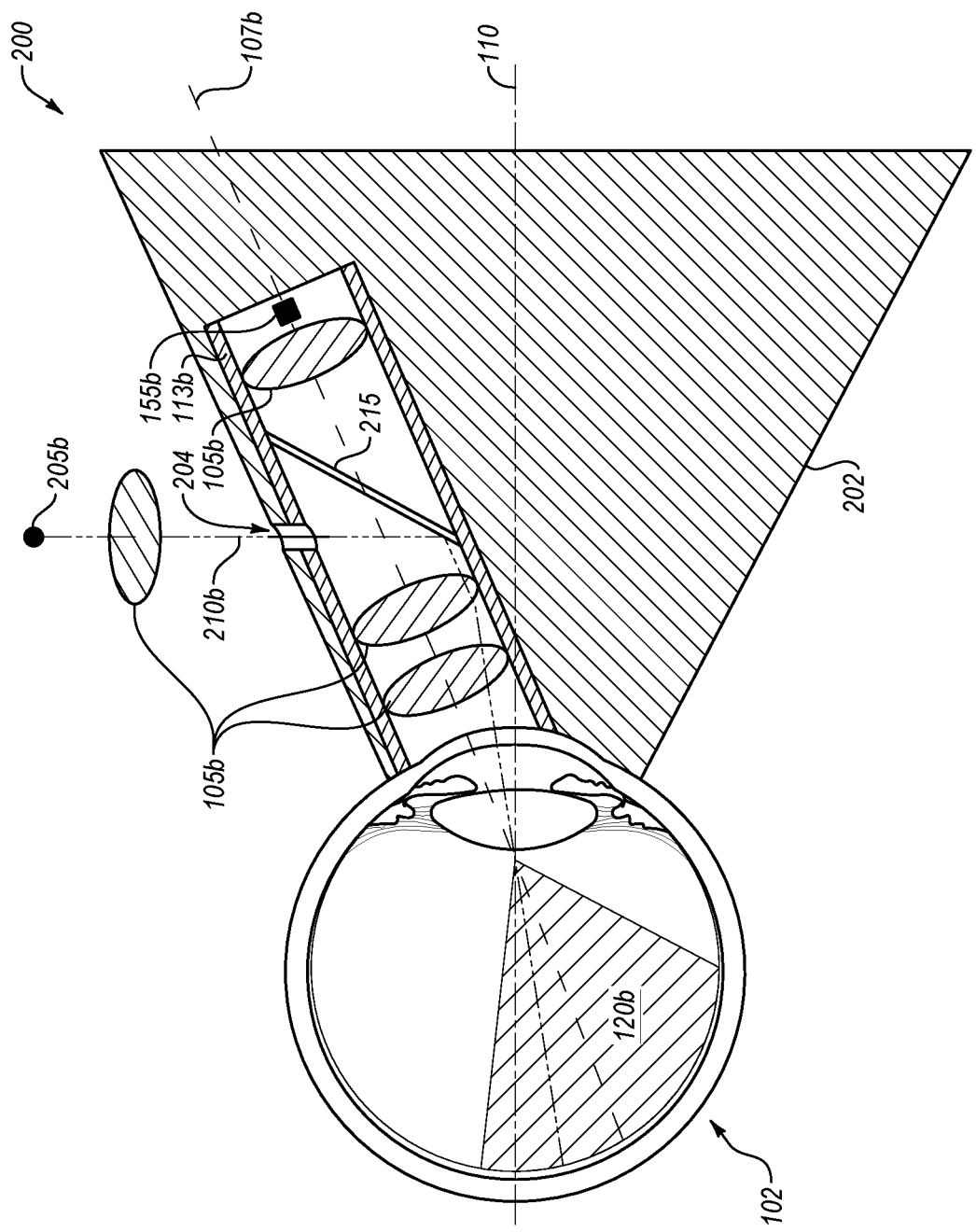
FIG. 2B illustrates another example embodiment of a cross-sectional side view of the optical imaging device of FIG. 2A using primary fixation for imaging the eye.

FIG. 2B illustrates another example embodiment of a cross-sectional side view of the optical imaging device 200 using primary fixation for imaging the eye 102, all arranged according to one or more embodiments of the present disclosure. As illustrated, the optical imaging device 200 includes the optical lenses 105b, the optical imaging pathway 107b, the imaging channel 113b, and the image capturing device 155b of FIGS. 1A-1B. Additionally, FIG. 2B illustrates the support structure 202 of FIG. 2A along with an optical byway 204, a primary fixation target 205b, a primary fixation target projection 210b, and a prism 215.

In some embodiments, the primary fixation target 205b and the primary fixation target projection 210b may be the same as or similar to the primary fixation target 205a and the primary fixation target projection 210a, respectively, of FIG. 2A. For example, the primary fixation target 205b may be positioned differently than the primary fixation target 205a of FIG. 2A, e.g., outside of the imaging channel 113b. In this manner, the primary fixation target projection 210b may proceed from the primary fixation target 205b, through one or more optical elements such as one of the optical lenses 105b, through the optical byway 204 to impinge the prism 215, through one or more additional optical elements such as the optical lenses 105b, and to the eye 102, e.g., onto a fovea of the eye 102.

In some embodiments, the prism 215 may be configured as a mirror, beam splitter, or other suitable reflective element (e.g., partially reflective, substantially reflective, or completely reflective). In these or other embodiments, multiple prisms 215 may be positioned within the imaging channel 113b, while in other embodiments, only a single prism 215 may be positioned within the imaging channel 113a. Additionally or alternatively, the prism 215 may help direct light to and/or from the eye 102, e.g., permitting multi-directional travel of optical signals between the eye 102 and the optical imaging device 200.

In some embodiments, the optical byway 204 may be a thru-hole between inside the imaging channel 113b and outside the support structure 202. Additionally or alternatively, the optical byway 204 may be configured as an optically transparent section of the support structure 202 and wall of the imaging channel 113b such that at least a portion of optical signals transmitted from the primary fixation target 205b passes through the optical byway 204 into the imaging channel 113b.

Modifications, additions, or omissions may be made to the embodiments of FIGS. 2A-2B without departing from the scope of the present disclosure. For example, in some embodiments, the channel 113b may include any number of other components that may not be explicitly illustrated or described.

Figure 3A:
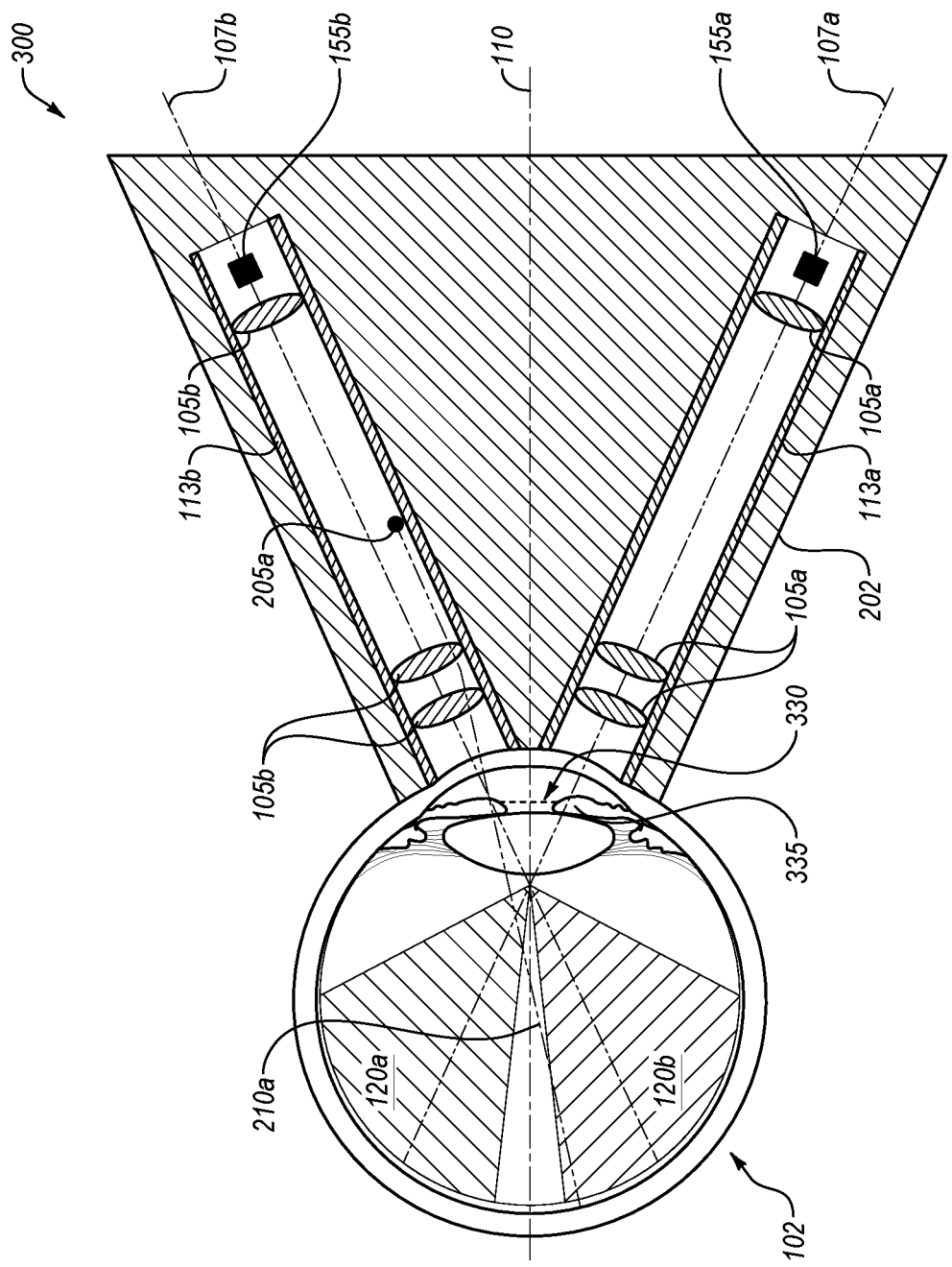
FIG. 3A illustrates an example embodiment of a cross-sectional side view of an optical imaging device using primary fixation for imaging the eye with an example small-pupil.

FIG. 3A illustrates an example embodiment of a cross-sectional side view of an optical imaging device 300 using primary fixation for imaging the eye 102 with an example small-pupil, all arranged according to one or more embodiments of the present disclosure. As illustrated, the optical imaging device 300 includes the optical lenses 105b, the optical imaging pathway 107b, the imaging channel 113b, the imaging region 120b, the image capturing device 155b, the support structure 202, the primary fixation target 205a, and the primary fixation target projection 210a of FIG. 2A in addition to the optical lenses 105a, the optical imaging pathway 107a, the imaging channel 113a, the imaging region 120a, and the image capturing device 155a of FIGS. 1A-1B. In these or other embodiments, when the eye 102 fixates on the primary fixation target 205a, the optical imaging device 300 may be aligned with the central axis 110 of the eye 102.

In some embodiments, a smaller size of the pupil (illustrated by plane 330 of the pupil) or larger size of an iris 335 may result in limited imaging capability using primary fixation with the primary fixation target 205a. For example, as illustrated, the optical imaging pathways 107a/107b may be at least partially obstructed by the iris 335 such that the imaging regions 120a/120b may be correspondingly reduced in size. Accordingly, in some embodiments, full imaging regions 120a/120b of the image capturing devices 155a/155b may correspond to the optical imaging pathways 107a/107b being unobstructed, e.g., by the iris 335. Additionally or alternatively, less than full imaging regions 120a/120b of the image capturing devices 155a/155b may correspond to the optical imaging pathways 107a/107b being at least partially obstructed. Thus, in some embodiments, the optical imaging pathways 107a/107b may be respective center axes of fields of view of the image capturing devices 155a/155b, and although a center portion of the fields of view may be obstructed (e.g., by the iris 335), other portions of the fields of view may proceed beyond the obstruction to image the imaging regions 120a/120b. In these or other embodiments, the imaging regions 120a/120b may not overlap in small-pupil scenarios. As referred to herein, a "small pupil" may include a pupil sized smaller than a minimum pupil diameter for multi-channel image acquisition of images having overlap for composite image generation. For example, a minimum pupil diameter may be in the closed range of 3 to 6 millimeters.

In some embodiments, the respective optical imaging pathways 107a/107b of the imaging channels 113a/113b may converge at a position within the anterior portion of the eye 102, for example, anterior to the plane 330 of the pupil or anterior to the equatorial line 117 of FIG. 1B. In these or other embodiments, when the respective optical imaging pathways 107a/107b cross anterior to the plane 330 of the pupil, each of the respective optical imaging pathways 107a/107b may acquire full images without clipping. For example, when the pupil of the eye 102 is dilated sufficiently, the optical imaging device 300 may acquire a composite optical image as a result of each of the respective optical imaging pathways 107a/107b fitting through the plane 330 of the pupil without being clipped.

In some embodiments, the respective imaging pathways may not cross the central axis 110 of the eye 102 anterior to the plane 330 of the pupil in the anterior chamber, but rather converge at a position in the posterior cavity 119 of FIG. 1B. In these embodiments, dilation of the eye 102 may be significant enough for the optical imaging pathways 107a/107b to fit through the plane 330 of the pupil without being clipped. However, in some cases the eye 102 may not dilate adequately for this purpose. In these or other embodiments, it may still be desirable to obtain an image of the eye 102, even if the image is not a composite wide-field image.

Figure 3B:
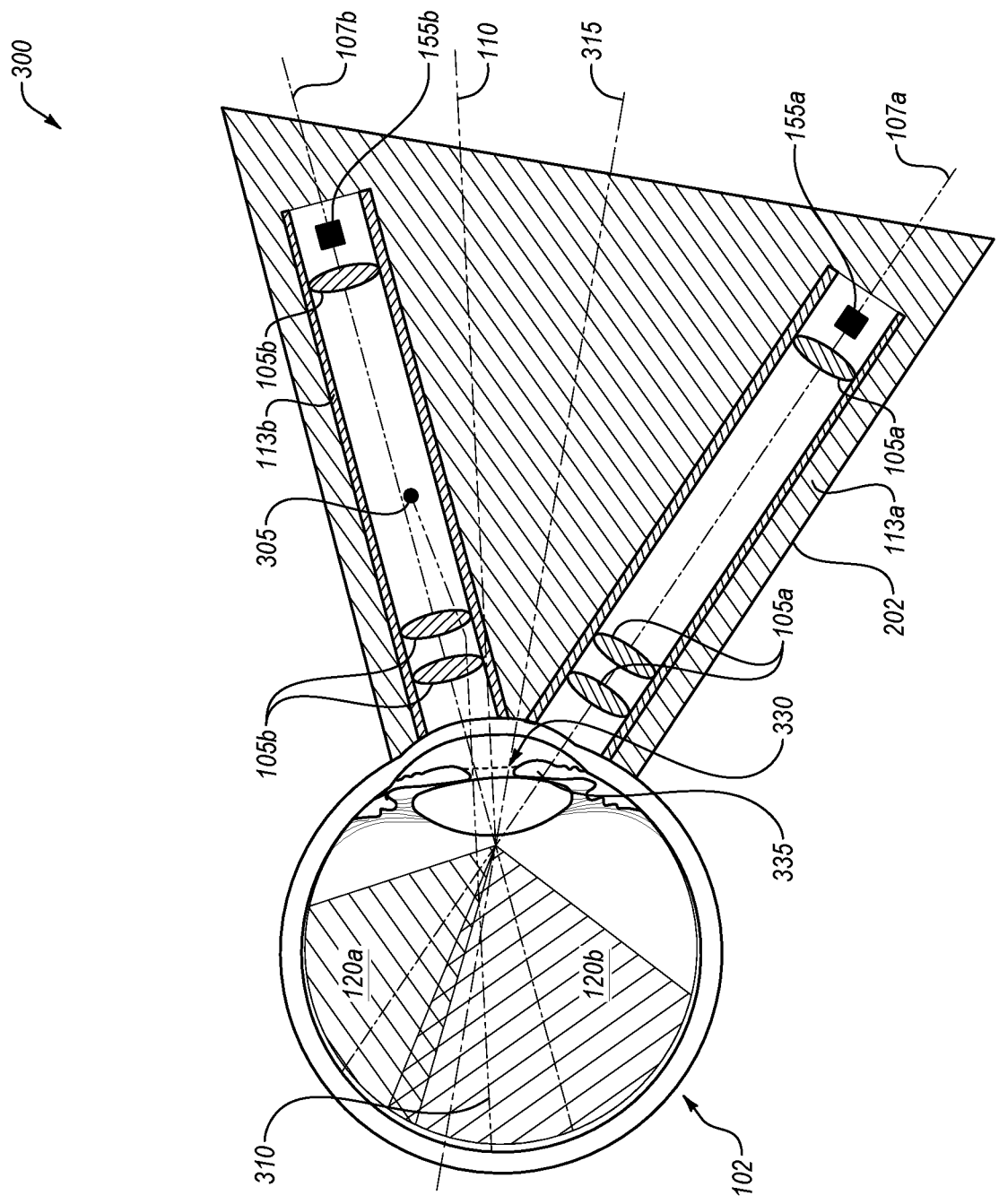
FIG. 3B illustrates another example embodiment of a cross-sectional side view of the optical imaging device of FIG. 3A using secondary fixation for imaging the eye with an example small-pupil.

FIG. 3B illustrates another example embodiment of a cross-sectional side view of the optical imaging device 300 using secondary fixation for imaging the eye 102 with an example small-pupil, all arranged according to one or more embodiments of the present disclosure. As illustrated, the optical imaging device 300 includes the optical lenses 105a/105b, the optical imaging pathways 107a/107b, the imaging channels 113a/113b, the imaging regions 120a/120b, the image capturing devices 155a/155b, and the support structure 202 of FIG. 3A in addition to a secondary fixation target 305, a secondary fixation target projection 310, and a center axis 315 of the support structure 202. In these or other embodiments, the secondary fixation target 305 and the secondary fixation target projection 310 may be the same as or similar to the primary fixation target 205a and the primary fixation target projection 210a, respectively, of FIG. 3A but differing positionally.

In some embodiments, secondary fixation may be implemented to more favorably position at least one imaging channel 113 relative to the eye 102 such that a greater portion of the eye 102 may be imaged. As illustrated in FIG. 3B, the imaging channel 113b may be more favorably oriented relative to the eye 102. In these or other embodiments, secondary fixation may be implemented using the secondary fixation target 305 and/or by moving the optical imaging device 300 such that the center axis 315 is not collinear with the central axis 110 of the eye 102. In this manner, the optical imaging pathway 107b may cross the plane 330 of the pupil at a closer distance to the central axis 110 of the eye 102 in comparison to the optical imaging pathway 107b of FIG. 3A.

For example, during secondary fixation of FIG. 3B, the imaging channel 113b may be positioned closer to the central axis 110 (relative to the imaging channel 113b during primary fixation in FIG. 3A), and the imaging channel 113a may be positioned farther away from the central axis 110 (relative to the imaging channel 113a during primary fixation in FIG. 3A). For instance, an angle of the imaging channel 113b may change relative to the central axis 110 of the eye 102 upon utilizing the secondary fixation target 305 by around 50 degrees or less, such as about 2-3 degrees, about 5-7 degrees, about 10-13 degrees, about 15-20 degrees, or in some cases between about 25 and 45 degrees. In these and other embodiments, while shifting the central axis 110 of the eye 102 such that one of the imaging channels 113 (e.g., the imaging channel 113b) may permit capturing of images without being clipped due to lack of pupil dilation, the other imaging channels (e.g., the imaging channel 113a) may be shifted further away from the central axis 110 of the eye 102 such images captured through the imaging channel 113a are even further clipped due to lack of pupil dilation and orientation of the imaging channel 113a. In some embodiments, the secondary fixation target 305 may be selected to facilitate a smaller number of the imaging channels 113 than is used for primary fixation to still be able to capture images, such as one, two, three, or other suitable number of imaging channels 113.

Additionally or alternatively, the secondary fixation target 305 may be positioned closer to the optical imaging pathway 107b relative to a position of the primary fixation target 205a in FIG. 3A. In these or other embodiments, by positioning the secondary fixation target 305 closer to wherever the optical imaging pathway 107b is, more favorable repositioning of the eye 102 may be induced for secondary fixation and image acquisition.

For example, in some embodiments, a greater amount of the eye 102 may be imaged in small-pupil scenarios when using secondary fixation. As illustrated in FIG. 3B, the imaging region 120b may increase in size relative to the imaging region 120b of FIG. 3A, and the imaging region 120a may decrease in size relative to the imaging region 120a of FIG. 3A. Additionally or alternatively for secondary fixation, the imaging region 120b may increase in a manner sufficient to overlap with the imaging region 120a, thereby permitting composite image generation. Additionally or alternatively for secondary fixation, the imaging region 120b may increase in size more than the imaging region 120a decreases in size. With increased amounts of the eye 102 able to be imaged using secondary fixation, more information about the eye 102 may be obtained than may be permitted in small-pupil scenarios with primary fixation.

Additionally or alternatively to the primary fixation target 205a and the secondary fixation target 305, in some embodiments, a movable fixation target may be configured to move along an axis between primary and secondary positions (where the primary and secondary fixation targets 205a/305 may be respectively positioned), for instance, moving back and forth along an axis so as to proceed closer to and farther from the eye 102. Additionally or alternatively, the movable fixation target may be configured to move along a different axis so as to proceed side-to-side and maintain relative distance to the eye 102. In some embodiments, the optical imaging device 300 may include multiple fixation targets, movable or stationary, or at least one secondary fixation target that moves in response to patient movement, eye movement, or movement of a doctor. Additionally or alternatively, the at least one secondary fixation target may move based on movement of optical components such as a prism.

In some embodiments, the image acquired with the imaging channel 113b using the secondary fixation target 305 may occur concurrently or near-concurrently with image acquisition by one or more other imaging channels, such as the imaging channel 113a. For example additional pictures may be taken with the other imaging channels by using rapid succession, by rotating or tilting the optical imaging device 300 for additional secondary fixation targets in the other imaging channels, and/or by having the patient look at or fixate on the additional secondary fixation targets in other imaging channels. The multiple images captured concurrently or near-concurrently may be stitched together for generating a composite image. Additionally or alternatively, the value of capturing various angles of the retina through the small pupil may be helpful and informative. In some embodiments, the imaging field of view and/or image quality with the single imaging channel may be reduced when utilized with the secondary fixation target 305.

Modifications, additions, or omissions may be made to the embodiments of FIGS. 3A-3B without departing from the scope of the present disclosure. For example, in some embodiments, the channels 113a/113b may include any number of other components that may not be explicitly illustrated or described. Additionally or alternatively, for example, the secondary fixation target 305 may be positioned in other locations than may be explicitly illustrated or described. Additionally or alternatively, for example, the secondary fixation target 305 may induce more or less movement of the eye 102 such that the central axis 110 deviates more or less from the center axis 315 of the support structure 202 than may be explicitly illustrated or described. Additionally or alternatively, for example, the support structure 202 may be rotated relative to the eye 102 more or less than may be explicitly illustrated or described during secondary fixation.

Figure 4:
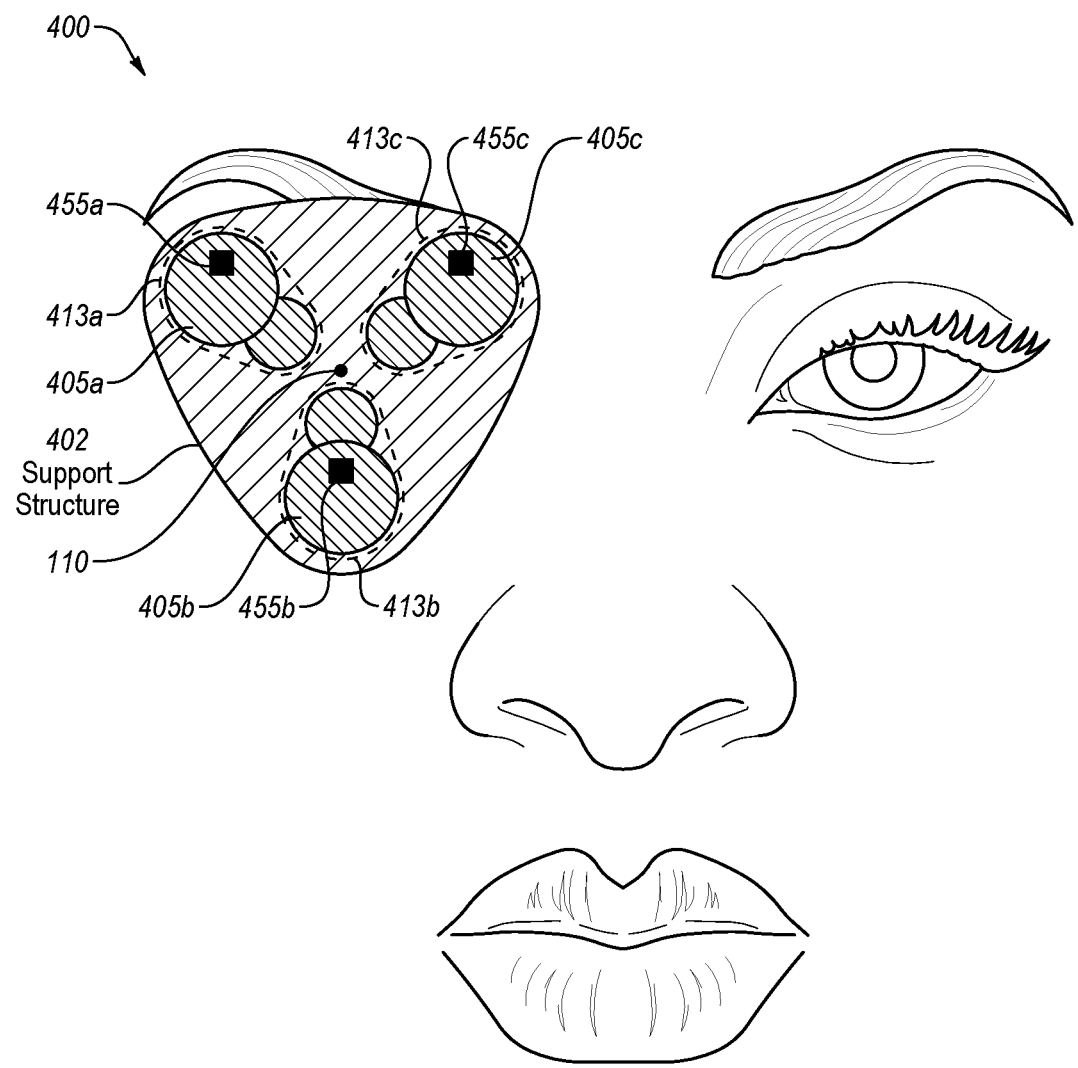
FIG. 4 illustrates a cross-sectional front view of an optical imaging device for imaging the eye, relative to facial features.

FIG. 4 illustrates a cross-sectional front view of an optical imaging device 400 for imaging the eye, relative to facial features, all arranged according to one or more embodiments of the present disclosure. As illustrated, the optical imaging device 400 includes a support structure 402, lenses 405a-405c, imaging channels 413a-413c, and image capturing devices 455a-455c. In some embodiments, the optical imaging device 400 may be aligned relative to a central axis 110 of an eye. Additionally or alternatively, the lenses 405a-405c, the imaging channels 413a-413c, and the image capturing devices 455a-455c may be the same as or similar to the lenses 105a-105b, the imaging channels 113a-113b, and the image capturing devices 255a-255b, respectively, of FIGS. 3A-3B.

The support structure 402 may be the same as or similar to the support structure 202 described above in conjunction with FIGS. 2A-2B and 3A-3B. In these or other embodiments, the support structure 402 may house the lenses 405a-405c, the imaging channels 413a-413c, and the image capturing devices 455a-455c. Additionally or alternatively, the support structure 402 may be sized and shaped for ergonomic purposes, e.g., to more suitably interface with facial features of a patient. In other embodiments, additional configurations of the support structure 402, other than an upside-down pyramidal configuration, may be implemented. For example, any suitable configuration permitting additional or increased clearance between the support structure 402 and one or both of a bony brow and a nose is contemplated herein. Additionally or alternatively, any suitable configuration permitting multiple imaging channels 413, e.g., two or more imaging channels 413, for imaging the eye may be implemented.

In some embodiments, the optical imaging device 400 may be rotated by rotating the support structure 402. For example, by rotating the support structure 402 in a clockwise or counter-clockwise direction about the central axis 110 of the eye, different portions of the eye may be imaged permitting different, and in some cases more favorable, orientations of the imaging channels 413 for imaging the eye 102 in small-pupil scenarios.

In some embodiments, more or fewer numbers of lenses 405 may be used within any of the imaging channels 413, e.g., to permit more suitable imaging of a particular area of the eye. Additionally or alternatively, the lenses 405 may be sized and shaped to fill an inner diameter of the imaging channels 413 that house the lenses 405, while in other embodiments, the lenses 405 may be sized and shaped to be less than the inner diameter of the imaging channel 413. Additionally or alternatively, one or more components may be positioned between, adjacent to, distal to, and/or proximal to any of the lenses 405.

In some embodiments, the imaging channels 413a-413c may be angled relative to each other. Additionally or alternatively, the imaging channels 413a-413c may be angled relative to the central axis 110 of the eye such that no imaging channel 413 may be coaxial with the central axis 110 of the eye. In other embodiments, at least one imaging channel 413 may be coaxial with the central axis 110 of the eye. The imaging channels 413a-413c may be sized, shaped and/or positioned within the support structure 402 in any suitable configuration, e.g., depending on an imaging application or pupil size of the eye to be imaged. Additionally or alternatively, the imaging channels 413a-413c may be sized, shaped and/or positioned relative to the eye, e.g., the central axis 110 of the eye depending on an imaging application or pupil size of the eye to be imaged.

Additionally or alternatively, more or fewer imaging channels 413 may be utilized in the optical imaging device 400, e.g., to facilitate up to three hundred and sixty degrees around the eye of image acquisition capability. For example, the optical imaging device 400 may include imaging channels 413 numbering between two and twelve imaging channels 413, such as between two and three, three and four, four and five, five and six, six and seven, seven and eight, eight and nine, or nine and ten. In some embodiments, more imaging channels 413 may be utilized to provide a more circumferential view of the eye while less imaging channels 413 may provide less of a circumferential view of the eye, given that each imaging channel 413 may only capture a portion of the eye. In these or other embodiments, the image capturing devices 455 may capture images all at the same time or in rapid succession, for example, using a rapid multi-plex. In this manner, for example, topographical information or a topographical profile may be generated at representative locations, e.g., at 12 o'clock, 2 o'clock, 4 o'clock, 6 o'clock, 8 o'clock, and 10 o'clock positions of the eye. Additionally or alternatively, one or more of the imaging channels 413 may be rotated relative to the support structure 402. For example, while the support structure 402 remains in a static position relative to the eye and/or facial features of the patient, any of the imaging channels 413 may be rotated inside the support structure 402. Such internal rotation of the imaging channels 413 may enable different portions of the eye to be imaged permitting the imaging of the eye in small-pupil scenarios described above in conjunction with FIGS. 3A-3B.

Modifications, additions, or omissions may be made to the embodiments of FIG. 4 without departing from the scope of the present disclosure. For example, in some embodiments, the support structure 402 may include any number of other components that may not be explicitly illustrated or described. Additionally or alternatively, the support structure 402 may be sized, shaped, and/or oriented relative to facial features in other suitable ways than may be explicitly illustrated or described. Additionally or alternatively, for example, the imaging channels 413a-413c may be sized, shaped, positioned, and/or oriented within the support structure 402 in other suitable ways than may be explicitly illustrated or described.

Figure 5:
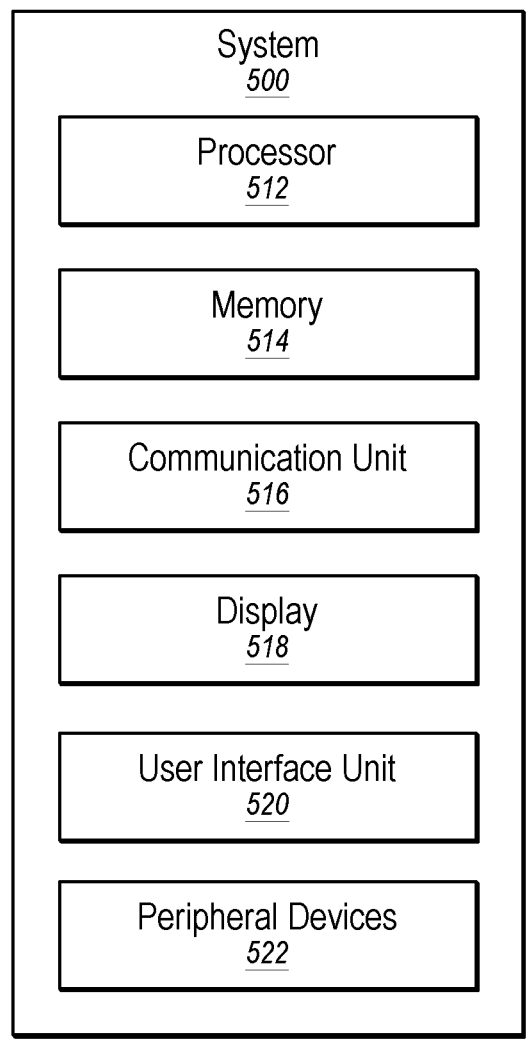
FIG. 5 illustrates an example system that may be used in multiple off-axis channel imaging of the eye.

FIG. 5 illustrates an example system 500 that may be used in multiple off-axis channel imaging of the eye. The system 500 may be arranged in accordance with at least one embodiment described in the present disclosure. The system 500 may include a processor 510, memory 512, a communication unit 516, a display 518, a user interface unit 520, and a peripheral device 522, which all may be communicatively coupled. In some embodiments, the system 500 may be part of any of the systems or devices described in this disclosure.

Generally, the processor 510 may include any suitable special-purpose or general-purpose computer, computing entity, or processing device including various computer hardware or software modules and may be configured to execute instructions stored on any applicable computer-readable storage media. For example, the processor 510 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data.

Although illustrated as a single processor in FIG. 5, it is understood that the processor 510 may include any number of processors distributed across any number of networks or physical locations that are configured to perform individually or collectively any number of operations described in this disclosure. In some embodiments, the processor 510 may interpret and/or execute program instructions and/or process data stored in the memory 512. In some embodiments, the processor 510 may execute the program instructions stored in the memory 512.

For example, in some embodiments, the processor 510 may execute program instructions stored in the memory 512 that are related to determining whether generated sensory data indicates an event and/or determining whether the event is sufficient to determine that the user is viewing a display of a device such that the system 500 may perform or direct the performance of the operations associated therewith as directed by the instructions. In these and other embodiments, instructions may be used to perform one or more operations or functions described in the present disclosure.

The memory 512 may include computer-readable storage media or one or more computer-readable storage mediums for carrying or having computer-executable instructions or data structures stored thereon. Such computer-readable storage media may be any available media that may be accessed by a general-purpose or special-purpose computer, such as the processor 510. By way of example, and not limitation, such computer-readable storage media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store particular program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 510 to perform a certain operation or group of operations as described in this disclosure. In these and other embodiments, the term "non-transitory" as explained in the present disclosure should be construed to exclude only those types of transitory media that were found to fall outside the scope of patentable subject matter in the Federal Circuit decision of *In re Nuijten,* 500 F.3d 1346 (Fed. Cir. 2007). Combinations of the above may also be included within the scope of computer-readable media.

The communication unit 516 may include any component, device, system, or combination thereof that is configured to transmit or receive information over a network. In some embodiments, the communication unit 516 may communicate with other devices at other locations, the same location, or even other components within the same system. For example, the communication unit 516 may include a modem, a network card (wireless or wired), an infrared communication device, a wireless communication device (such as an antenna), and/or chipset (such as a Bluetooth device, an 802.6 device (e.g., Metropolitan Area Network (MAN)), a Wi-Fi device, a WiMax device, cellular communication facilities, etc.), and/or the like. The communication unit 516 may permit data to be exchanged with a network and/or any other devices or systems described in the present disclosure.

The display 518 may be configured as one or more displays, like an LCD, LED, or other type of display. For example, the display 518 may be configured to present measurements, indicate warning notices, show tolerance ranges, display whether good/bad eye tissues are determined, and other data as directed by the processor 510.

The user interface unit 520 may include any device to allow a user to interface with the system 500. For example, the user interface unit 520 may include a mouse, a track pad, a keyboard, buttons, and/or a touchscreen, among other devices. The user interface unit 520 may receive input from a user and provide the input to the processor 510. In some embodiments, the user interface unit 520 and the display 518 may be combined.

The peripheral devices 522 may include one or more devices. For example, the peripheral devices may include a sensor, a microphone, and/or a speaker, among other peripheral devices. As examples, the sensor may be configured to sense changes in light, sound, motion, rotation, position, orientation, magnetization, acceleration, tilt, vibration, etc., e.g., as relating to an eye of a patient. Additionally or alternatively, the sensor may be part of or communicatively coupled to the optical imaging device as described in the present disclosure.

Modifications, additions, or omissions may be made to the system 500 without departing from the scope of the present disclosure. For example, in some embodiments, the system 500 may include any number of other components that may not be explicitly illustrated or described. Further, depending on certain implementations, the system 500 may not include one or more of the components illustrated and described.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner. Additionally, the term "about" or "approximately" should be interpreted to mean a value within 10% of actual value.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner. Additionally, the terms "about," "substantially," and "approximately" should be interpreted to mean a value within 10% of an actual value, for example, values like 3 mm or 100% (percent).

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

What is claimed is:

1. An optical imaging device, comprising:
   a support structure; and
   a plurality of imaging channels, each imaging channel of the plurality of imaging channels including a discrete optical imaging pathway, the plurality of imaging channels disposed within the support structure, the plurality of imaging channels aimed at different angles relative to each other such that each optical imaging pathway is directed towards a pupil of an eye; and
   a secondary fixation target within at least one imaging channel of the plurality of imaging channels, the secondary fixation target configured to enable at least one corresponding optical imaging pathway to fit through a pupil diameter of the pupil that is smaller than a minimum pupil diameter for multi-channel image acquisition if using a primary fixation target, the minimum pupil diameter representative of a diameter below which at least one of the imaging channels would be at least partially obstructed if using the primary fixation target.

2. The optical imaging device of claim 1, further comprising the primary fixation target, the primary fixation target positioned inside at least one imaging channel of the plurality of imaging channels.

3. The optical imaging device of claim 2, wherein a fixation target projection of the primary fixation target and an optical imaging pathway of the at least one imaging channel shares one or more common optical lenses.

4. The optical imaging device of claim 1, wherein a fixation target projection of the primary fixation target impinges a prism.

5. The optical imaging device of claim 1, further comprising:
   a plurality of image capturing devices, each image capturing device of the plurality of image capturing devices respectively associated with one of the plurality of imaging channels to capture digital photograph images of respective portions of the eye.

6. The optical imaging device of claim 1, further comprising:
   a plurality of sets of optical lenses, at least one lens in each of the sets of optical lenses having a fixed position within a respective imaging channel of the plurality of imaging channels.

7. The optical imaging device of claim 1, wherein the secondary fixation target is configured to induce movement of the eye such that an optical imaging pathway of at least one imaging channel of the plurality of imaging channels passes through a plane of the pupil at a closer distance to a central axis of the eye than if using the primary fixation target.

8. The optical imaging device of claim 1, wherein the secondary fixation target is configured to induce a shift of a central axis of the eye, relative to at least a first imaging channel of the plurality of imaging channels, by 50 degrees or less.

9. The optical imaging device of claim 8, wherein the secondary fixation target is configured to induce the shift of the central axis of the eye such that an optical imaging pathway of a second imaging channel is at least partially obstructed from passing through the pupil of the eye.

10. The optical imaging device of claim 1, wherein the minimum pupil diameter is in a range of between 3 and 6 millimeters.

11. The optical imaging device of claim 1, wherein:
   the support structure includes a support structure axis;
   the support structure axis is coaxial with a central axis of the eye if using the primary fixation target; and
   the support structure axis is non-coaxial with the central axis of the eye when using the secondary fixation target.

12. The optical imaging device of claim 1, further comprising:

a primary fixation target position located outside of the plurality of imaging channels or positioned inside at least one imaging channel of the plurality of imaging channels;

a secondary fixation target position located within the at least one imaging channel of the plurality of imaging channels; and a moving fixation target configured to move along an axis between the primary fixation target position and the secondary fixation target position.

13. The optical imaging device of claim 12, wherein the moving fixation target is configured to move along the axis between the primary fixation target position and the secondary fixation target position such that the moving fixation target moves either one or both of closer to and farther away from the eye.

14. The optical imaging device of claim 12, wherein the moving fixation target is configured to move along the axis between the primary fixation target position and the secondary fixation target position such that the moving fixation target moves laterally relative to the eye and maintains an approximately constant distance from the eye.

15. A system comprising:

one or more processors configured to receive optical imaging data; and an optical imaging device configured to generate optical imaging data, the optical imaging device communicatively coupled to the one or more processors, and the optical imaging device comprising:

a support structure; and a plurality of imaging channels, each imaging channel of the plurality of imaging channels including a discrete optical imaging pathway, the plurality of imaging channels disposed within the support structure, the plurality of imaging channels aimed at different angles relative to each other such that each optical imaging pathway is directed towards a pupil of an eye; and a secondary fixation target within at least one imaging channel of the plurality of imaging channels, the secondary fixation target configured to enable at least one corresponding optical imaging pathway to fit through a pupil diameter of the pupil that is smaller than a minimum pupil diameter for multi-channel image acquisition if using a primary fixation target, the minimum pupil diameter representative of a diameter below which at least one of the imaging channels would be at least partially obstructed if using the primary fixation target.

16. The system of claim 15, wherein:

the support structure includes a support structure axis;

the support structure axis is coaxial with a central axis of the eye during primary fixation; and the support structure axis is non-coaxial with the central axis of the eye during secondary fixation.

17. The system of claim 15, wherein the secondary fixation target is configured to induce movement of the eye such that an optical imaging pathway of at least one imaging channel of the plurality of imaging channels passes through a plane of the pupil at a closer distance to a central axis of the eye than if using the primary fixation target.

18. The system of claim 15, wherein the secondary fixation target is configured to induce a shift of a central axis of the eye, relative to at least a first imaging channel of the plurality of imaging channels, by 50 degrees or less.

19. The system of claim 18, wherein the secondary fixation target is configured to induce the shift of the central axis of the eye such that an optical imaging pathway of a second imaging channel is at least partially obstructed from passing through the pupil of the eye.

20. The system of claim 15, wherein the minimum pupil diameter is in a range of between 3 and 6 millimeters.

* * * * *